United States Patent
Kato et al.

(10) Patent No.: US 11,923,138 B2
(45) Date of Patent: Mar. 5, 2024

(54) COLLECTING DEVICE AND COLLECTING METHOD

(71) Applicant: Kioxia Corporation, Tokyo (JP)

(72) Inventors: Sho Kato, Mie (JP); Yuji Yamada, Mie (JP); Jiahong Wu, Mie (JP)

(73) Assignee: KIOXIA CORPORATION, Tokyo (JP)

( * ) Notice: Subject to any disclaimer, the term of this patent is extended or adjusted under 35 U.S.C. 154(b) by 188 days.

(21) Appl. No.: 17/682,934

(22) Filed: Feb. 28, 2022

(65) Prior Publication Data
US 2023/0070820 A1 Mar. 9, 2023

(30) Foreign Application Priority Data
Sep. 9, 2021 (JP) .................. 2021-146835

(51) Int. Cl.
| | | |
|---|---|---|
| *H01F 7/20* | (2006.01) | |
| *G01N 1/02* | (2006.01) | |
| *G01N 1/04* | (2006.01) | |
| *G01N 33/202* | (2019.01) | |
| *H01F 1/44* | (2006.01) | |
| *H01J 49/10* | (2006.01) | |
| *B01D 11/02* | (2006.01) | |
| *G01N 1/10* | (2006.01) | |
| *G01N 1/40* | (2006.01) | |
| *G01N 33/00* | (2006.01) | |
| *H01J 49/00* | (2006.01) | |

(52) U.S. Cl.
CPC ................. *H01F 7/20* (2013.01); *G01N 1/04* (2013.01); *G01N 33/202* (2019.01); *H01F 1/44* (2013.01); *H01J 49/105* (2013.01)

(58) Field of Classification Search
CPC .... H01F 7/20; H01F 1/44; G01N 1/04; G01N 33/202; G01N 2001/4038; G01N 1/10; G01N 2001/028; G01N 2001/1006; G01N 1/02; G01N 33/00; G01N 2033/0095; H01J 49/105; H01J 49/00; B01D 11/0211
See application file for complete search history.

(56) References Cited

U.S. PATENT DOCUMENTS

| | | | |
|---|---|---|---|
| 5,676,877 A | 10/1997 | Borduz et al. | |
| 6,261,471 B1 | 7/2001 | Tsuda et al. | |
| 2019/0376881 A1* | 12/2019 | Rackus | ............. B01L 3/502761 |

FOREIGN PATENT DOCUMENTS

| | | |
|---|---|---|
| JP | S62-160719 A | 7/1987 |
| JP | H10-004006 A | 1/1998 |
| JP | 2003-524293 A | 8/2003 |
| JP | 2008-159657 A | 7/2008 |
| JP | 2008-300605 A | 12/2008 |

* cited by examiner

*Primary Examiner* — Herbert K Roberts
*Assistant Examiner* — Anthony W Megna Fuentes
(74) *Attorney, Agent, or Firm* — Foley & Lardner LLP (57) ABSTRACT

A collecting device includes a stage configured to place a substrate. A magnetic field generating unit holds, by a magnetic field, a first liquid containing a magnetic fluid and a collecting liquid to bring the first liquid into contact with at least an end portion of the substrate. A collecting unit collects the first liquid from the magnetic field generating unit. A separating unit separates the collecting liquid from the first liquid.

20 Claims, 6 Drawing Sheets

COLLECTING DEVICE AND COLLECTING METHOD

FIELD

Embodiments described herein generally relate to a collecting device and a collecting method.

BACKGROUND

Contamination of a semiconductor device by an unwanted metal causes performance degradation of the semiconductor device or a defect in a manufacturing process of the semiconductor device. To identify a cause and location of defects due to such metal contamination, a metal analyzing apparatus such as inductively coupled plasma-mass spectrometry (ICP-MS) may be used. The metal analyzing apparatus collects metal contaminants by wiping a measurement target portion on the semiconductor device with a wiping member impregnated with a liquid, or sweeps the semiconductor device with a liquid and collects the liquid containing the metal contaminants, thereby performing a mass analysis on metal components contained in the collected liquid.

To collect metal with a liquid, a method for wiping a measurement target portion of a semiconductor device with a wiping member or a method for sweeping a surface of a semiconductor device with a liquid held in a nozzle may be used. By these methods in the related art, however, it is difficult to accurately and automatically collect metal at an end portion (a bevel portion) of the semiconductor device.

DETAILED DESCRIPTION

Embodiments provide a collecting device and a collecting method that can accurately and automatically collect an impurity on an end portion of a semiconductor device.

In general, according to one embodiment, a collecting device includes a stage configured to place a substrate. A magnetic field generating unit (generator) holds, by a magnetic field, a first liquid containing a magnetic fluid and a collecting liquid to bring the first liquid into contact with at least an end portion of the substrate. A collecting unit (collector) collects the first liquid from the magnetic field generating unit. A separating unit (separator) separates the collecting liquid from the first liquid.

Hereinafter, embodiments according to the present disclosure will be described with reference to the drawings. The present disclosure is not limited to the embodiments. The drawings are schematic or conceptual drawings. Ratios or the like between elements are not necessarily the same as actual ones. In the specification and the drawings, the same elements as those described in preceding drawings are denoted by the same reference numerals, and a detailed description is omitted as appropriate.

First Embodiment

Figure 1:
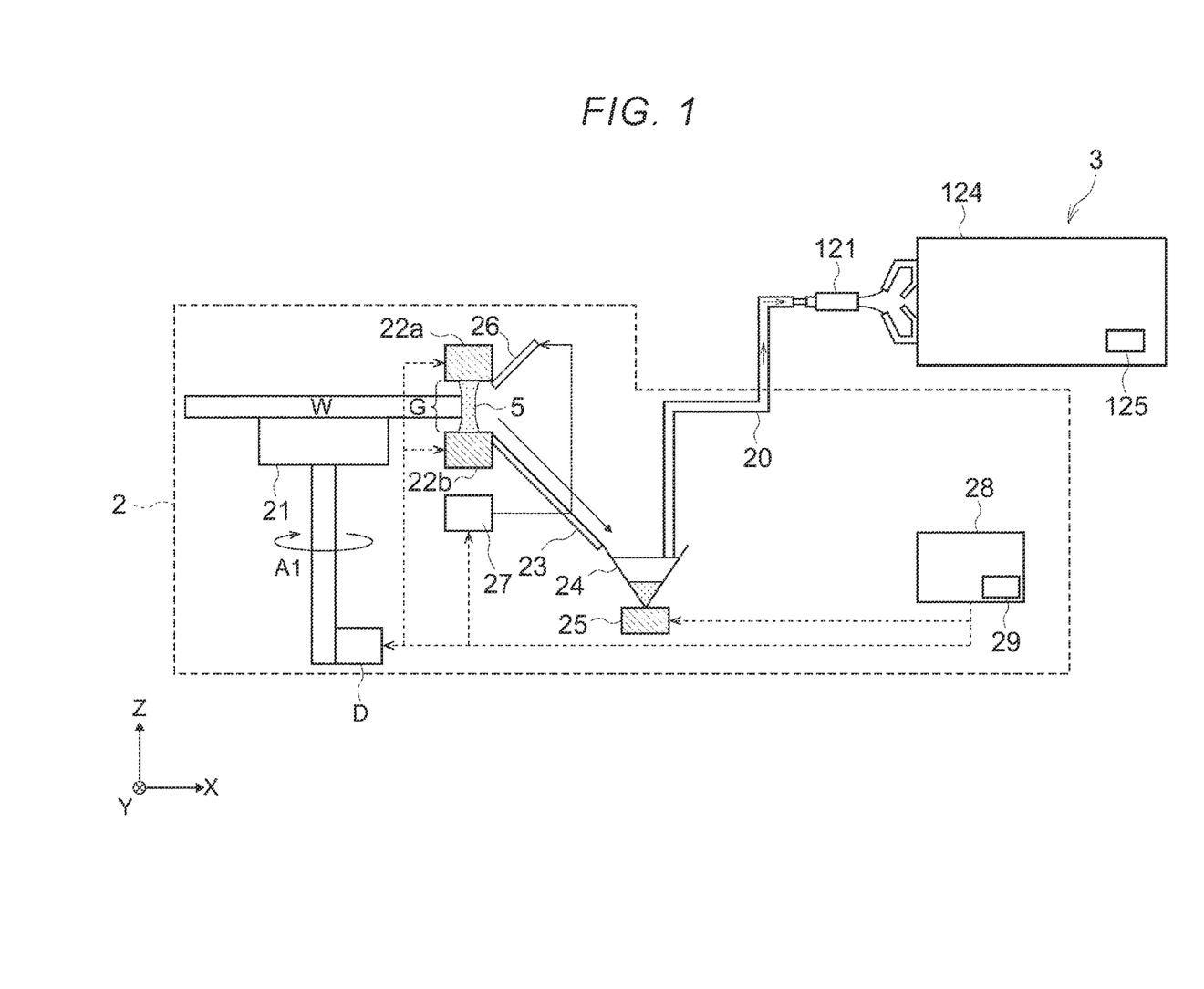
FIG. 1 is a block diagram showing a configuration example of a metal analyzing apparatus according to a first embodiment.

FIG. 1 is a block diagram showing a configuration example of a metal analyzing apparatus 1 according to the first embodiment. The metal analyzing apparatus 1 may be an analyzing apparatus such as ICP-MS. A flow of data or control signals is indicated by a dashed arrow. A flow of a liquid is indicated by a solid arrow.

The metal analyzing apparatus 1 includes a collecting device 2 and an analyzing device 3. The collecting device 2 includes a stage 21, magnetic field generating units 22a, 22b, 25, a collecting unit 23, a container 24, a liquid supplying unit (supply) 26, a liquid storing unit 27, a controller 28, and a memory 29. The collecting device 2 may be in a normal pressure atmosphere or a reduced-pressure atmosphere.

A semiconductor substrate W is placeable on the stage 21, and the stage 21 can rotate the semiconductor substrate W in a direction indicated by an arrow A1. The stage 21 is rotationally driven by a driving unit D. The driving unit D is controlled by the controller 28.

The magnetic field generating unit 22a and the magnetic field generating unit 22b are disposed next to the stage 21 while facing each other in a Z direction (substantially vertical direction). A gap G between the magnetic field generating unit 22a and the magnetic field generating unit 22b (i.e., a distance between surfaces facing each other) is at substantially the same level as a height of the semiconductor substrate W on the stage 21. The gap G is wider than the semiconductor substrate W in a thickness direction so that the magnetic field generating unit 22a and the magnetic field generating unit 22b do not come into contact with the semiconductor substrate W. Therefore, the semiconductor substrate W can be inserted into the gap G by relatively moving the stage 21 or the magnetic field generating units 22a and 22b in an X direction (substantially horizontal direction).

The magnetic field generating unit 22a and the magnetic field generating unit 22b hold, by a magnetic field, a liquid 5 containing a magnetic fluid and a collecting liquid in the gap G. The liquid 5 is in contact with at least an end portion (a bevel portion) of the semiconductor substrate W when the semiconductor substrate W is inserted into the gap G. By rotating the semiconductor substrate W while the liquid 5 being in contact with the end portion of the semiconductor substrate W, a metal contaminant on the end portion of the semiconductor substrate W can be eluted and taken into the liquid 5.

The magnetic field generating units 22a and 22b are, for example, electromagnets, and a magnetic field applied to the gap G is controlled by the controller 28. For example, when predetermined power is supplied to the magnetic field generating units 22a and 22b under the control of the controller 28, the magnetic field generating units 22a and 22b are turned on, and a magnetic field of a predetermined intensity is generated in the gap G. The liquid 5 can be held to be continuous between the magnetic field generating unit 22a and the magnetic field generating unit 22b by controlling the intensity of the magnetic field by the controller 28. That is, the liquid 5 can counter its own weight by the magnetic field and be held in the gap G. On the other hand, when the power to the magnetic field generating units 22a and 22b is cut off and the magnetic field generating units 22a and 22b are turned off, the magnetic field in the gap G disappears. Therefore, the liquid 5 is not held in the gap G and flows down into the collecting unit 23 by its own weight.

The liquid 5 contains a magnetic fluid and a collecting liquid. The magnetic fluid is a fluid in which magnetic particles are dispersed in a liquid by adsorbing a surfactant onto ferromagnetic particles or paramagnetic particles. The ferromagnetic particles or the paramagnetic particles may be, for example, magnetite ($Fe_3O_4$) particles, iron particles, and cobalt particles. The particle diameter of the ferromagnetic particles or the paramagnetic particles is, for example, about 10 nm. The surfactant is prepared with oleic acid and the like as raw materials, and is adsorbed onto the ferromagnetic particles or the paramagnetic particles to form one or two layers of coatings to prevent aggregation of the ferromagnetic particles or the paramagnetic particles. Further, the ferromagnetic particles or the paramagnetic particles need to have a coating that has resistance against an acidic environment or an acidic liquid.

The magnetic fluid is a liquid that reacts to a magnetic field, and a shape and position of the magnetic fluid can be controlled to some extent by applying a magnetic field. Therefore, a shape and position of the liquid 5 obtained by mixing the collecting liquid with the magnetic fluid can be controlled to some extent by applying a magnetic field. A viscosity of the magnetic fluid is enough to allow the magnetic fluid to retain its shape according to a magnitude of the magnetic field under an environment in which the magnetic field is applied.

The collecting liquid is a liquid that dissolves a substance (for example, metal) to be subjected to mass analysis. The collecting liquid is not particularly limited, and may be, for example, a liquid containing one of HF, HCL, $HNO_3$, and $H_2O_2$. When the metal contaminant is, for example, Na or the like having a low oxidation reduction potential, the collecting liquid may be a mixture of HF and $H_2O$. When the metal contaminant has low collection efficiency in the mixture of HF and $H_2O$ (for example, Cu, Ag, etc. having a high oxidation reduction potential), a mixture of HF, HCL and $H_2O_2$ or a mixture of HF, $HNO_3$ and HCl may be used as the collecting liquid.

Concentrations of the magnetic fluid and the collecting liquid in the liquid 5 are to such a degree that the shapes can be retained in response to the magnetic field and the metal contaminant can be dissolved. For example, the concentration of the magnetic fluid in the liquid 5 can be approximately 10 wt % and the concentration of the collecting liquid can be appropriately adjusted from a few tenth wt % to tens of wt % depending on an element type of metal contaminant.

The ferromagnetic particles or the paramagnetic particles may be repeatedly used by separating the collecting liquid from the liquid 5 and then taking out only the ferromagnetic particles or the paramagnetic particles from the magnetic fluid and cleaning them. Therefore, a cost needed for the liquid 5 can be reduced.

The substance to be subjected to mass analysis may be any element as long as the element is a metal.

The collecting unit 23 is an instrument that couples the magnetic field generating units 22a and 22b and the container 24 of a separating unit to flow the liquid 5 from the magnetic field generating units 22a and 22b to the container 24. For example, the collecting unit 23 may be a U-shaped or V-shaped gutter or a cylindrical tube. The collecting unit 23 is a non-magnetic member and is made of a material that has corrosion resistance against the liquid 5. For example, the collecting unit 23 is made of a non-magnetic fluorine resin.

The container 24 is an instrument that retains the liquid 5 from the collecting unit 23. The container 24 is a non-magnetic member and is made of a material that has corrosion resistance against the liquid 5. For example, the container 24 is made of a non-magnetic fluorine resin and has a bowl shape. The container 24 serves as a separating unit in cooperation with the magnetic field generating unit 25. The container 24 is not particularly limited, and has a shape such as an inverted cone shape or an inverted polygonal pyramid shape such that an opening of the container 24 is wide and gradually decreases toward a bottom.

The magnetic field generating unit 25 applies, from the outside of the container 24, a magnetic field to the liquid 5 retained in the container 24. Similar to the magnetic field generating units 22a and 22b, the magnetic field generating unit 25 is, for example, an electromagnet, and the magnetic field applied to the liquid 5 is controlled by the controller 28. For example, when predetermined power is supplied to the magnetic field generating unit 25 under the control of the controller 28, the magnetic field generating unit 25 is turned on, and a magnetic field of a predetermined intensity is generated. The magnetic field generating unit 25 unevenly distributes the magnetic fluid of the liquid 5 in the container 24 by applying the magnetic field to the liquid 5, thereby separating the magnetic fluid from the collecting liquid. For example, the magnetic field generating unit 25 attracts the magnetic fluid to the bottom of the container 24, and conversely, separates the collecting liquid to an upper portion of the container 24. The collecting liquid is separated independently from the magnetic fluid as a supernatant in the container 24.

The magnetic field generating unit 25 generates a magnetic field having an intensity that enables the liquid 5 to be divided into the magnetic fluid and collecting liquid. On the other hand, the magnetic field generating units 22a and 22b generate a magnetic field having an intensity that enables the liquid 5 to be held in the gap G without being divided into the magnetic fluid and collecting liquid. Therefore, the magnetic field generating unit 25 generates a stronger magnetic field than the magnetic field generating units 22a and 22b, and applies this magnetic field to the liquid 5.

The liquid supplying unit 26 supplies the liquid 5 to the magnetic field generating units 22a and 22b. For example, the liquid supplying unit 26 is connected to the liquid storing unit 27 that stores the liquid 5 through a piping, suctions the liquid 5 from the liquid storing unit 27, and supplies the liquid 5 to the gap between the magnetic field generating unit 22a and the magnetic field generating unit 22b. At this time, when the magnetic field generating units 22a and 22b apply the magnetic field to the gap G, the liquid 5 can be held in the gap G.

The liquid supplying unit 26 may be a tubular body through which the liquid 5 passes. The liquid storing unit 27 may be a container capable of storing the liquid 5. The liquid supplying unit 26 and the liquid storing unit 27 are non-magnetic members and are made of a material that has corrosion resistance against the liquid 5. For example, the liquid supplying unit 26 and the liquid storing unit 27 is made of a non-magnetic fluorine resin.

A piping 20 connects the container 24 and the analyzing device 3, and conveys the collecting liquid from the container 24 to the analyzing device 3. A pump (not shown) is provided in the piping 20 so that the collecting liquid can be conveyed from the container 24 to the analyzing device 3. The piping 20 is a non-magnetic member and is made of a material that has corrosion resistance against the liquid 5. For example, the piping 20 is made of a non-magnetic fluorine resin.

The analyzing device (for example, ICP-MS device) 3 includes a plasma torch 121 and a mass analyzing unit 124. The analyzing device 3 vaporizes and quantitatively analyzes the collecting liquid to specify a content of a metal (element) to be analyzed contained in the collecting liquid. The plasma torch 121 vaporizes the collecting liquid from the piping 20, mixes the vaporized collecting liquid with a carrier gas, and ionizes this mixture with plasma. The mass analyzing unit 124 detects a signal intensity (spectrum) of an element of an impurity contained in the collecting liquid from the ionized gas. The mass analyzing unit 124 detects ions of the impurity and performs quantitative analysis based on the detection result. The mass analyzing unit 124 includes a calculating unit 125 that executes calculation based on result data obtained by the quantitative analysis. For example, a computer or the like may be used for the calculating unit 125. In the embodiment, the analyzing device 3 is used, and the analyzing device 3 may use an ICP-optical emission spectrometer (ICP-OES) in addition to the ICP-MS device. In this case, an ICP-OES unit specifies the content of the element of the impurity based on a light wavelength (spectrum) obtained from the vaporized collecting liquid. The element to be analyzed is, for example, an element such as silicon or metal.

The controller 28 may be a personal computer or a semiconductor chip such as a CPU. The controller 28 may be provided in the collecting device 2, and may be provided separately from the collecting device 2. Further, the controller 28 may be provided in the analyzing device 3.

The memory 29 stores information about a rotation speed of the stage 21, information about the power supplied to the magnetic field generating units 22a, 22b, and 25, information about an amount of the liquid 5 supplied from the liquid supplying unit 26, and the like. The memory 29 also stores coordinate information on the semiconductor substrate W, a sequence showing a magnetic field generating operation of the magnetic field generating units 22a, 22b, and 25, and the like. The memory 29 also stores a program for controlling the collecting device 2. These information in the memory 29 are used for the controller 28 to control each component of the collecting device 2. The memory 29 may be a hard disk drive (HDD), a solid state drive (SSD), or the like.

Next, a collecting method for the liquid 5 will be described.

Figure 2:
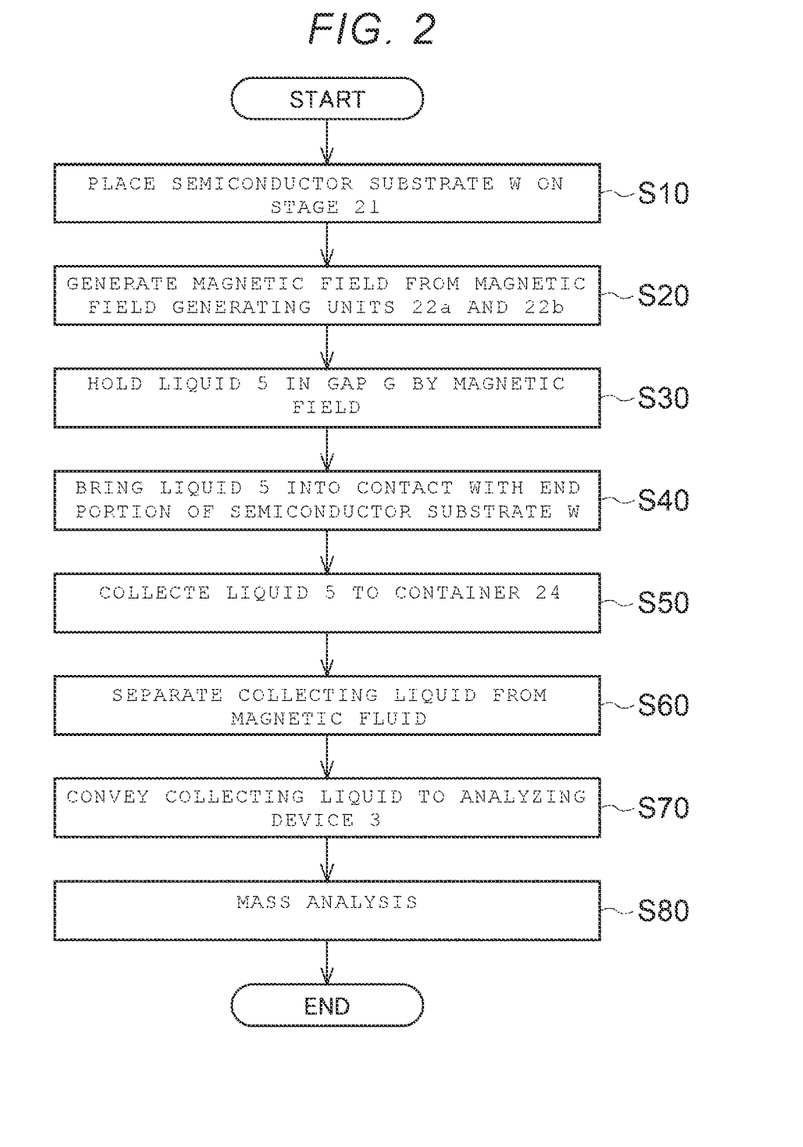
FIG. 2 is a flow chart showing an example of a collecting method for a liquid according to at least one embodiment.

FIG. 2 is a flow chart showing an example of the collecting method for the liquid 5 according to the embodiment.

First, the semiconductor substrate W is placed on the stage 21 (S10).

Then, power is supplied to the magnetic field generating units 22a and 22b to generate a magnetic field (S20). The magnetic field generating units 22a and 22b generate the magnetic field in the gap G.

Figure 4:
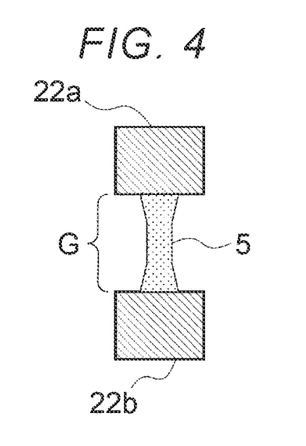
FIG. 4 is a diagram showing a state of a liquid between magnetic field generating units.

Then, the liquid supplying unit 26 supplies a predetermined amount of the liquid 5 to the gap G between the magnetic field generating units 22a and 22b. The liquid supplying unit 26 may supply the liquid 5 to an upper surface of the magnetic field generating unit 22b. As shown in FIG. 4, the magnetic field generating units 22a and 22b hold the liquid 5 continuously in the gap G by the magnetic field (S30). FIG. 4 is a diagram showing a state of the liquid 5 between the magnetic field generating unit 22a and the magnetic field generating unit 22b. The controller 28 adjusts the magnetic field of the magnetic field generating units 22a and 22b so that the liquid 5 is held in the gap G.

Figure 5:
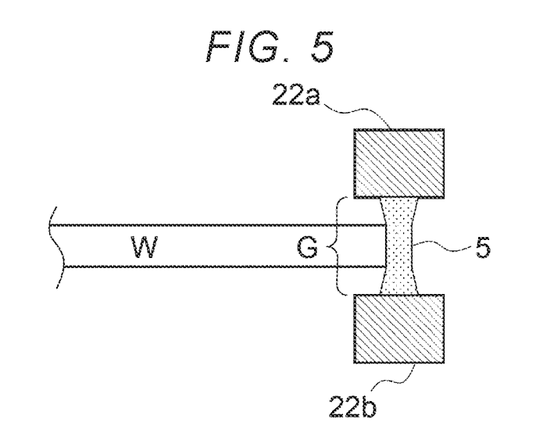
FIG. 5 is a diagram showing a state in which the liquid is in contact with an end portion of a semiconductor substrate.

Then, while the stage 21 rotates the semiconductor substrate W, the end portion (bevel portion) of the semiconductor substrate W is inserted into the gap G. Therefore, as shown in FIG. 5, the liquid 5 is brought into contact with the end portion of the semiconductor substrate W (S40). FIG. 5 is a diagram showing a state in which the liquid 5 is in contact with the end portion of the semiconductor substrate W. A rotation speed of the semiconductor substrate W is a speed at which the liquid 5 is not blown off and the liquid 5 can sweep the end portion, and is about 7 mm/sec. At this time, the liquid 5 contains the collecting liquid, and thus can dissolve and take in the metal contaminant adhering to the end portion of the semiconductor substrate W. Since the semiconductor substrate W and the liquid 5 may be moved relatively to each other, the liquid 5 may be rotationally moved with respect to a periphery of the semiconductor substrate W. The liquid 5 may be moved to be close to the semiconductor substrate W. That is, the magnetic field generating units 22a and 22b may be moved with respect to the semiconductor substrate W.

The semiconductor substrate W may be further inserted into the gap G, and a front surface and a back surface of the semiconductor substrate W may be swept with the liquid 5. Therefore, the collecting device 2 can also dissolve and take in the metal contaminant on the front surface and the back surface of the semiconductor substrate W. When the semiconductor substrate W is inserted into the gap G, the liquid 5 is separated by a front surface side and a back surface side of the semiconductor substrate W, and is held in the gap G by the magnetic field. The sweeping of the end portion (bevel portion) of the semiconductor substrate W and the sweeping of the front surface and the back surface of the semiconductor substrate W may be performed individually using different liquids 5. Therefore, the detection of the impurity on the end portion of the semiconductor substrate W and the detection of the impurity on the front surface and the back surface of the semiconductor substrate W may be performed individually. On the other hand, the entire surface including the end portion of the semiconductor substrate W may be swept with the liquid 5. Therefore, the impurity on the entire semiconductor substrate W can be detected.

In this way, the liquid 5 is in contact with the end portion of the semiconductor substrate W for predetermined time while rotating the semiconductor substrate W. Therefore, the impurity on the end portion of the semiconductor substrate W can be collected by sweeping the end portion of the semiconductor substrate W with the liquid 5. Then, the semiconductor substrate W is separated from the liquid 5, and the rotation of the semiconductor substrate W is stopped.

Figure 6:
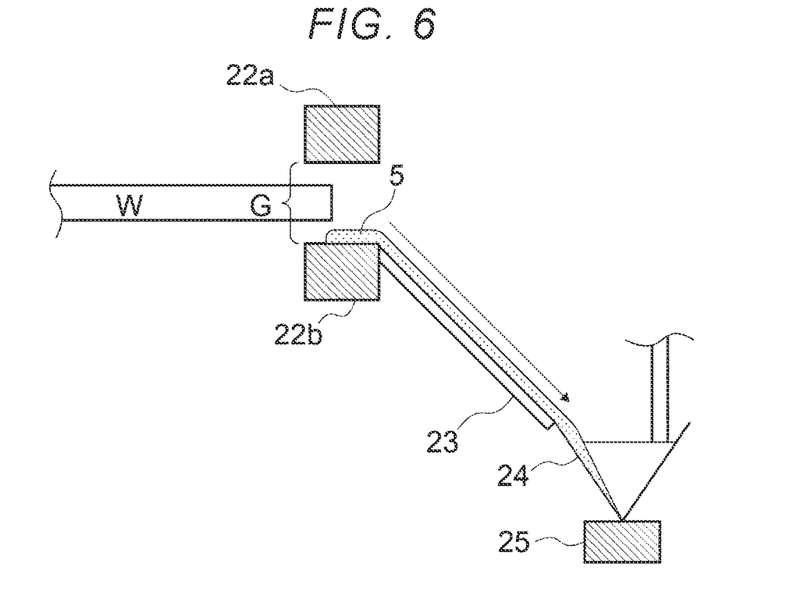
FIG. 6 is a diagram showing a state in which the liquid is collected into a container.

Then, the power supplied to the magnetic field generating unit 22b is increased, and the power supplied to the magnetic field generating unit 22a is reduced or stopped. Therefore, the magnetic field generating unit 22a weakens or stops the magnetic field, and the magnetic field generating unit 22b strengthens the magnetic field to attract the liquid 5. Therefore, the liquid 5 is unevenly distributed toward the magnetic field generating unit 22b by the magnetic field of the magnetic field generating unit 22b and the own weight of the liquid 5. Further, as shown in FIG. 6, the liquid 5 is collected to the container 24 through the collecting unit 23 by stopping the power supply of the magnetic field generating unit 22a (S50). FIG. 6 is a diagram showing a state in which the liquid 5 is collected in the container 24. Alternatively, by supplying the power to the magnetic field generating unit 25, the liquid 5 may be attracted to the container 24 by the magnetic field of the magnetic field generating unit 25.

Figure 7:
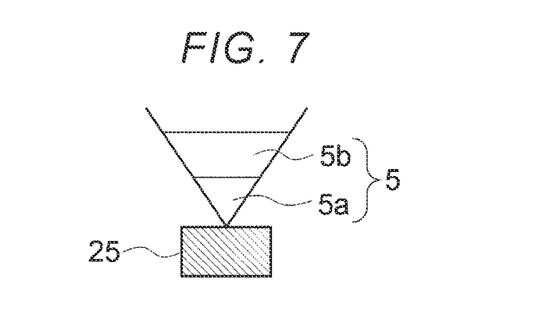
FIG. 7 is a diagram showing a state in which a collecting liquid is separated from a magnetic fluid.

Then, power is supplied to the magnetic field generating unit 25 to generate a magnetic field. As shown in FIG. 7, the magnetic field generating unit 25 attracts a magnetic fluid 5a and unevenly distributes the magnetic fluid 5a of the liquid 5 in the container 24 by applying the magnetic field to the liquid 5 collected in the container 24. In FIG. 7, the magnetic fluid is attracted to the bottom of the container 24, and conversely, a collecting liquid 5b moves upward and is separated from the magnetic fluid 5a (S60). FIG. 7 is a diagram showing a state in which the collecting liquid 5b is separated from the magnetic fluid 5a.

Figure 8:
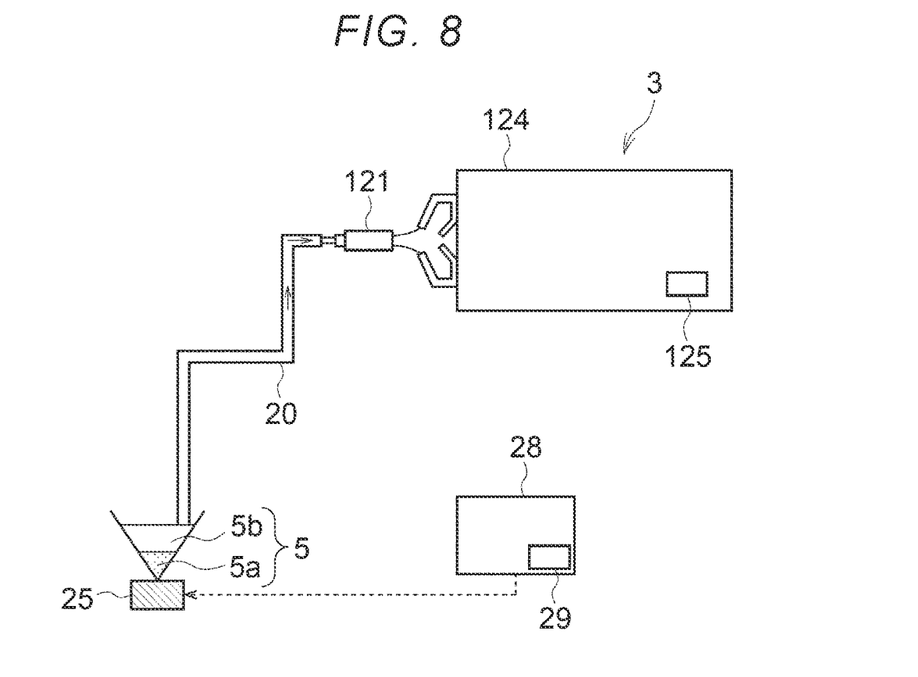
FIG. 8 is a diagram showing a state in which the collecting liquid is conveyed to an analyzing device.

Then, as shown in FIG. 8, the piping 20 conveys only the separated collecting liquid 5b to the analyzing device 3 (S70). FIG. 8 is a diagram showing a state in which the collecting liquid 5b is conveyed to the analyzing device 3. The collecting liquid 5b contains the metal contaminant adhering to the end portion of the semiconductor substrate W. Ratios of amounts of the magnetic fluid 5a and the collecting liquid 5b contained in the liquid 5 are predetermined. A supply amount of the liquid 5 is also predetermined. Further, a shape and volume of the container 24 is also known in advance. Therefore, a height position of the separated collecting liquid 5b in the container 24 is almost known. When an opening end of the piping 20 is disposed at a predetermined height position of the container 24, only the separated collecting liquid 5b can be conveyed to the analyzing device 3.

The collecting liquid 5b is separated from the liquid 5 and then only the ferromagnetic particles or the paramagnetic particles may be taken out from the magnetic fluid 5a and be cleaned. Therefore, the ferromagnetic particles or the paramagnetic particles can be repeatedly used.

Thereafter, the analyzing device 3 performs mass analysis on the collecting liquid 5b (S80). The analyzing device 3 performs mass analysis on the impurity contained in the collecting liquid 5b based on the signal intensity of the element obtained from the collecting liquid 5b.

According to the embodiment, the liquid 5 is a liquid containing the magnetic fluid 5a and the collecting liquid 5b, and is a liquid in which the magnetic fluid 5a is given a function as the collecting liquid 5b. The liquid 5 can be held in the gap G between the magnetic field generating units 22a and 22b by applying a magnetic field to the liquid 5 by the magnetic field generating units 22a and 22b. Therefore, by rotating the semiconductor substrate W while the liquid 5 being in contact with the end portion (bevel portion) of the semiconductor substrate W, the impurity on the end portion of the semiconductor substrate W can be taken into the liquid 5.

When the collecting liquid is collected using a wiping member, collecting work is complicated and cannot be automated. Other impurities are easily mixed into the collecting liquid of the wiping member, which hinders accurate mass analysis.

When the collecting liquid sweeps the front surface of the semiconductor substrate W by a nozzle and the semiconductor substrate W is hydrophilic, even if trying to collect the impurity only on the end portion of the semiconductor substrate W, the collecting liquid is dragged to the front surface of the semiconductor substrate W and an impurity on the front surface of the semiconductor substrate W are also collected. Therefore, it is difficult to collect the impurity only on the end portion of the semiconductor substrate W.

In contrast, according to at least one embodiment, the liquid 5 can be held by the magnetic field in the gap G between the magnetic field generating units 22a and 22b, and the liquid 5 can be brought into contact with the end portion (bevel portion) of the semiconductor substrate W. In this case, even the semiconductor substrate W is hydrophilic, the impurity on the end portion of the semiconductor substrate W alone can be taken into the liquid 5. The collecting device 2 can automatically supply, hold, and collect the liquid 5. Further, the collecting device 2 can also automatically separate the collecting liquid from the liquid 5, and it is possible to prevent introduction of other extra impurities since no wiping member is used. In order to separate (extract) the collecting liquid, a magnetic field is used, and other solvents are not necessary. Therefore, since an impurity concentration in the collecting liquid does not decrease, the mass analysis of the impurities can be accurately performed.

(First Modification)

Figure 3A:
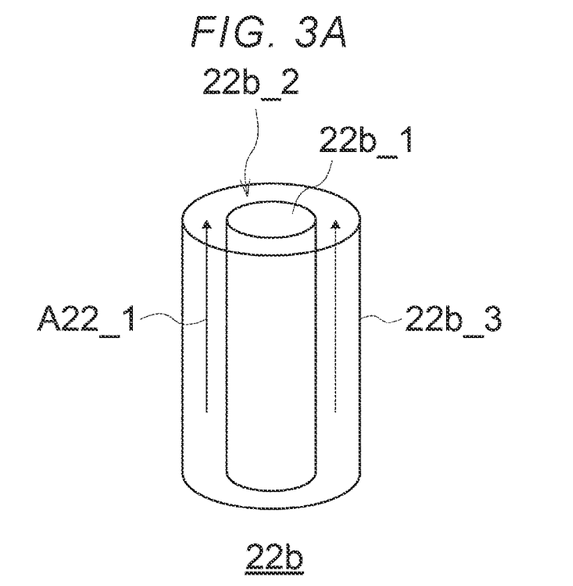
FIG. 3A is a perspective view showing a configuration example of a magnetic field generating unit according to a first modification of at least one embodiment.

FIG. 3A is a perspective view showing a configuration example of the magnetic field generating unit 22b according to the first modification of the embodiment. The magnetic field generating unit 22a may have the same configuration as that in the first embodiment. Alternatively, the magnetic field generating unit 22a may have the same configuration as that of the magnetic field generating unit 22b in FIG. 3A.

The magnetic field generating unit 22b according to the first modification also serves as a liquid supplying unit, and can both generate a magnetic field and supply the liquid. For example, the magnetic field generating unit 22b includes a columnar body 22b_1 that generates a magnetic field in a central portion, and a tubular body 22b_3 provided around the columnar body 22b_1. A hollow cavity 22b_2 through which the liquid 5 passes is defined between the columnar body 22b_1 and the tubular body 22b_3.

The columnar body 22b_1 and/or the tubular body 22b_3 generates the magnetic field by receiving power supply. The liquid 5 is supplied from the cavity 22b_2 onto the columnar body 22b_1 as indicated by an arrow A22_1. Therefore, the magnetic field generating unit 22a and the magnetic field generating unit 22b can hold the liquid 5 therebetween.

According to the first modification, the liquid supplying unit 26 is not necessary. In addition, since the magnetic field generating unit 22b and the liquid supplying unit are integrated, the liquid 5 can be reliably supplied onto the magnetic field generating unit 22b.

(Second Modification)

Figure 3B:
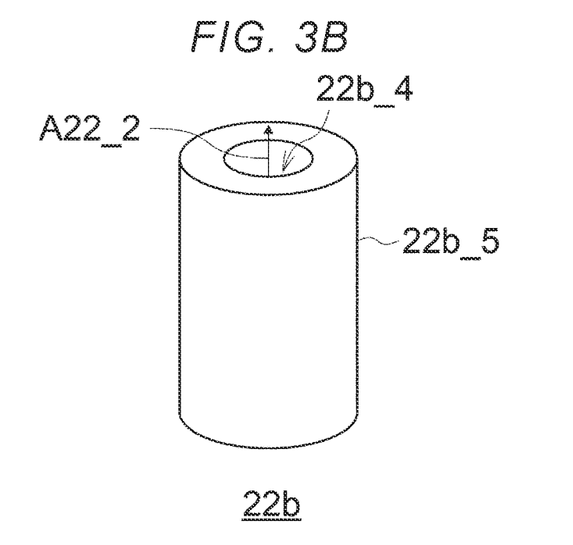
FIG. 3B is a perspective view showing a configuration example of a magnetic field generating unit (generator) according to a second modification of at least one embodiment.

FIG. 3B is a perspective view showing a configuration example of the magnetic field generating unit 22b according to the second modification of the embodiment. The magnetic field generating unit 22a may have the same configuration as that in the first embodiment. Alternatively, the magnetic field generating unit 22a may have the same configuration as that of the magnetic field generating unit 22b in FIG. 3B.

The magnetic field generating unit 22b according to the second modification also serves as a liquid supplying unit, and can both generate a magnetic field and supply the liquid. For example, the magnetic field generating unit 22b includes a hollow cavity 22b_4 that allows the liquid 5 to pass through a central portion. A tubular body 22b_5 that generates a magnetic field is provided around the cavity 22b_4. The tubular body 22b_5 is thick, and is able to sufficiently apply a magnetic field at an opening end. That is, the magnetic field generating unit 22b is the tubular body 22b_5 having the hollow cavity 22b_4 that allows the liquid 5 to pass through the central portion.

The tubular body 22b_5 generates the magnetic field by receiving power supply. The liquid 5 is supplied from the cavity 22b_4 onto the opening end of the tubular body 22b_5 as indicated by an arrow A22_2. Therefore, the magnetic field generating unit 22a and the magnetic field generating unit 22b can hold the liquid 5 therebetween.

According to the second modification, the liquid supplying unit 26 is not necessary. In addition, since the magnetic field generating unit 22b and the liquid supplying unit are integrated, the liquid 5 can be reliably supplied onto the magnetic field generating unit 22b.

While certain embodiments have been described, these embodiments have been presented by way of example only, and are not intended to limit the scope of the disclosure. Indeed, the novel embodiments described herein may be embodied in a variety of other forms; furthermore, various omissions, substitutions and changes in the form of the embodiments described herein may be made without departing from the spirit of the disclosure. The accompanying claims and their equivalents are intended to cover such forms or modifications as would fall within the scope and spirit of the disclosure.

What is claimed is:

1. A collecting device comprising:
   a stage configured to support a substrate;
   a magnetic field generator configured to hold, by a magnetic field, a first liquid containing a magnetic fluid and a collecting liquid, and to bring the first liquid into contact with at least an end portion of the substrate;
   a collector configured to collect the first liquid from the magnetic field generator; and
   a separator configured to separate the collecting liquid from the first liquid.

2. The collecting device according to claim 1, wherein the magnetic field generator includes a first magnetic field generator and a second magnetic field generator arranged to face each other, and
   the first and second magnetic field generators hold the first liquid such that the first liquid is continuous between the first magnetic field generator and the second magnetic field generator.

3. The collecting device according to claim 2, wherein a gap between the first magnetic field generator and the second magnetic field generator is wider than the substrate in a thickness direction of the substrate.

4. The collecting device according to claim 2, wherein the separator includes: a container configured to retain the first liquid from the collector, and a third magnetic field generator configured to apply, from an outside of the container, a magnetic field to the first liquid.

5. The collecting device according to claim 4, wherein the third magnetic field generator is configured to unevenly distribute the magnetic fluid of the first liquid in the container by applying a magnetic field to the first liquid, thereby separating the magnetic fluid from the collecting liquid.

6. The collecting device according to claim 5, wherein the third magnetic field generator is configured to apply a magnetic field to attract the magnetic fluid to a bottom of the container.

7. The collecting device according to claim 4, wherein the third magnetic field generator is configured to apply a stronger magnetic field than that of the first and second magnetic field generators to the first liquid.

8. The collecting device according to claim 4, wherein the container is non-magnetic.

9. The collecting device according to claim 1, wherein
   the collector is an instrument that connects the magnetic field generator and the separator to cause the first liquid to flow from the magnetic field generator to the separator.

10. The collecting device according to claim 1, further comprising:
    a supply configured to supply the first liquid to the magnetic field generator.

11. The collecting device according to claim 10, wherein the magnetic field generator is arranged to function as the supply.

12. The collecting device according to claim 1, wherein
    the magnetic field generator is a tubular body through which the first liquid passes.

13. The collecting device according to claim 1, wherein the end portion of the substrate has a bevel shape.

14. The collecting device according to claim 1, wherein the magnetic field generator includes a columnar body.

15. The collecting device according to claim 14, wherein the magnetic field generator includes a tubular body around the columnar body.

16. The collecting device according to claim 1, wherein the collector is non-magnetic.

17. The collecting device according to claim 1, wherein the magnetic field generator includes a plurality of electromagnets.

18. The collecting device according to claim 1, further comprising a controller configured to control the magnetic intensity of the magnetic field generator.

19. An analyzing apparatus comprising:
    the collecting device of claim 1; and
    an analyzing device arranged to receive and analyze the collecting liquid.

20. A collecting method using a collecting device, the collecting device including a stage configured to support a substrate, a magnetic field generator configured to hold a first liquid containing a magnetic fluid and a collecting liquid by a magnetic field, a collector configured to collect the first liquid from the magnetic field generator, and a separator configured to separate the collecting liquid from the first liquid, the collecting method comprising:
    holding the first liquid with the magnetic field generator by generating a magnetic field;
    bringing the first liquid into contact with at least an end portion of the substrate;
    stopping the magnetic field of the magnetic field generator and collecting the first liquid from the magnetic field generator to the separator through the collector; and
    separating the collecting liquid from the first liquid, in the separator.

* * * * *